United States Patent [19]

Sumikama et al.

[11] 3,971,246
[45] July 27, 1976

[54] METHOD AND APPARATUS FOR MEASURING THE COEFFICIENT OF THERMAL CONDUCTIVITY OF A SAMPLE

[75] Inventors: Sadao Sumikama; Nobuyoshi Tanaka; Yoshiaki Arakawa; Katsushi Akama, all of Tokyo, Japan

[73] Assignee: Showa Denko Kabushiki Kaisha, Tokyo, Japan

[22] Filed: Dec. 13, 1973

[21] Appl. No.: 424,276

[30] Foreign Application Priority Data

Dec. 21, 1972 Japan.............................. 47-127653
Sept. 26, 1973 Japan.............................. 48-108178
Sept. 26, 1973 Japan.............................. 48-107514

[52] U.S. Cl................................................. 73/15 A
[51] Int. Cl.²....................................... G01N 25/18
[58] Field of Search .................. 73/1 F, 15 A, 15 R, 73/75, 190 H, 193 R, 193 A

[56] References Cited
UNITED STATES PATENTS

| | | | |
|---|---|---|---|
| 3,045,473 | 7/1962 | Hager, Jr. ............................. | 73/15 A |
| 3,279,239 | 10/1966 | Arends et al. ....................... | 73/15 A |
| 3,576,472 | 4/1971 | Mashall............................... | 73/15 A |
| 3,592,060 | 7/1971 | Laverman........................... | 73/15 A |
| 3,605,494 | 9/1971 | Progelhof et al. ................ | 73/190 H |
| 3,822,580 | 7/1974 | Jamet et al.......................... | 73/15 R |

FOREIGN PATENTS OR APPLICATIONS

| | | | |
|---|---|---|---|
| 127,846 | 4/1958 | U.S.S.R................................ | 73/15 A |
| 149,256 | 10/1959 | U.S.S.R................................ | 73/15 A |

OTHER PUBLICATIONS

*International Dictionary of Physics and Electronics*; W. C. Michels, Sr. Ed.; D Van Nostrand Co., Inc; N.J.; 1956, pp. 416, 897–899.
Tentative Method of Test for Thermal Conductivity of Cellular Plastics by Means of a Probe; ASTM D2326–64T (issued 1964).
Zierfuss, H., *An Apparatus for the Rapid Determination of Heat Conductivity of Poor Conductors* in J. Sci. Instrum. vol. 40, pp. 69–71, Feb. 1963.

*Primary Examiner*—Richard C. Queisser
*Assistant Examiner*—John S. Appleman
*Attorney, Agent, or Firm*—Paul & Paul

[57] ABSTRACT

The coefficient of thermal conductivity of any sample can be measured without any pre-processing to the sample by putting an electric heater and a thermo-electric couple between a block made of reference material whose coefficient of thermal conductivity is known and the sample, flowing electric current in said heater, measuring the temperature of said heater with said thermo-couple, and calculating the coefficient of thermal conductivity of the sample according to the measured data. The present inventors introduce herein a novel equation for that calculation.

4 Claims, 18 Drawing Figures

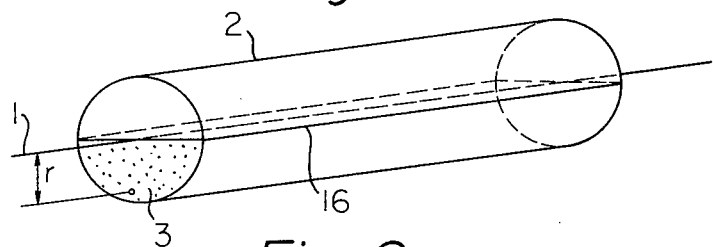
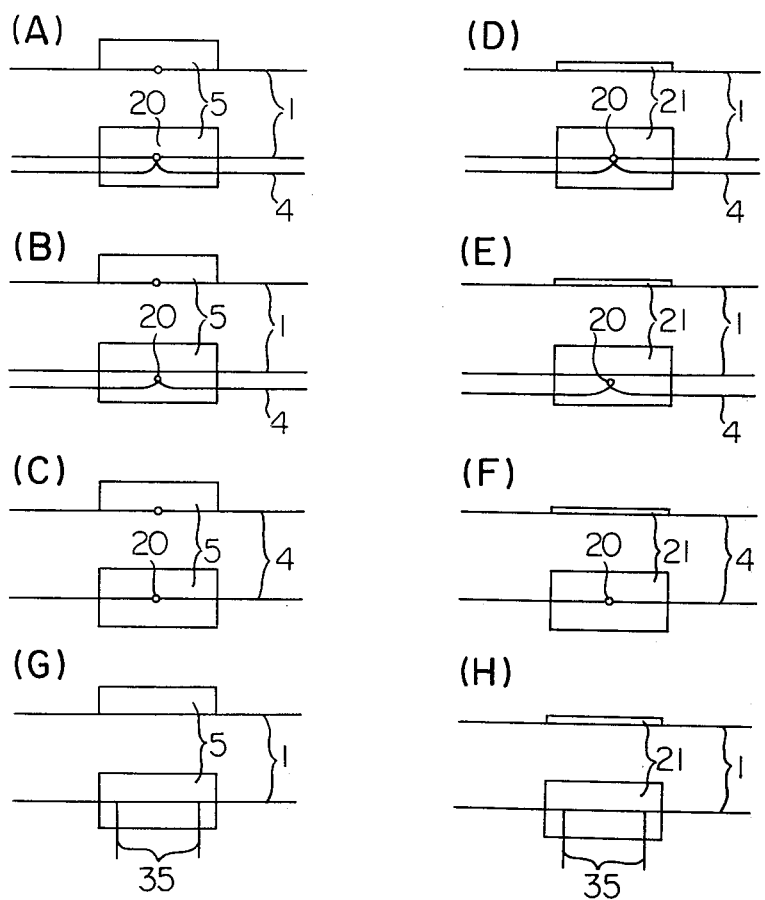

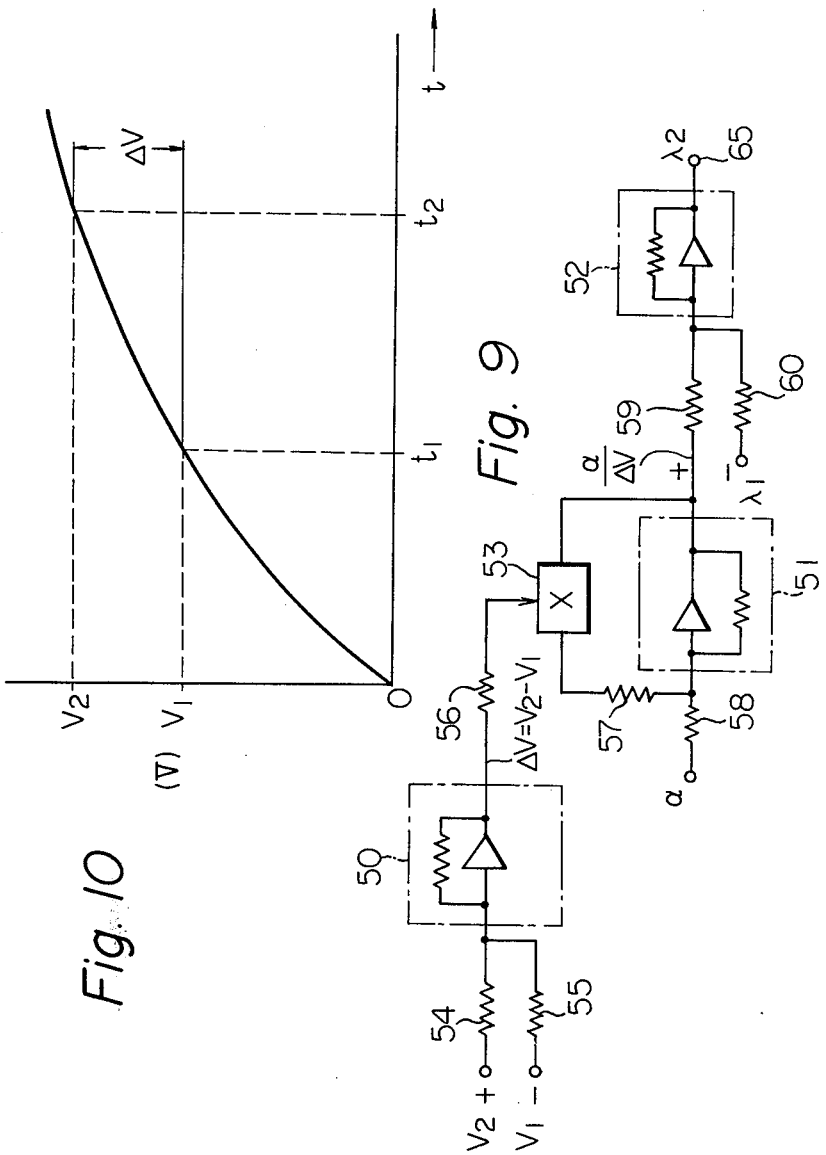

METHOD AND APPARATUS FOR MEASURING THE COEFFICIENT OF THERMAL CONDUCTIVITY OF A SAMPLE

BACKGROUND OF THE INVENTION

The present invention relates to a method and an apparatus for measuring the coefficient of thermal conductivity of any material and, in particular, relates to a method and an apparatus which provide said measurement with a simple and quick operation without any pre-processing of the material to be measured.

The coefficient of thermal conductivity of a material, like adiabatic material and a heat insulating material, is an important physical factor for evaluating the characteristics of the material. However, the prior art for measuring the coefficient of thermal conductivity has the following undesirable problems.

a. The prior measuring apparatus for the coefficient of thermal conductivity is complicated in operation, and requires a skilled operator.

b. The prior measuring apparatus for the coefficient of thermal conductivity requires a long time to measure said coefficient and, further, the measured result is not accurate.

c. The prior measurng apparatus for the coefficient of thermal conductivity requires the sample to be processed in a particular shape and length, however, some materials are hard to so process and consequently, the sample for measuring is not easily obtained.

d. According to the prior art, it is difficult to insert the sample in a measuring apparatus with heat equilibrium and no disturbance of heat condition.

e. According to the prior art, it is almost impossible to measure the coefficient of thermal conductivity of some material, like concrete or structural material, which is a part of a building.

The object of the present invention is to provide a method and an apparatus which overcome the above-mentioned drawbacks.

A further object of the present invention is to provide a method and an apparatus which can measure the coefficient of thermal conductivity of any material including brick, wood, glass, concrete and plastics without any pre-processing of a sample.

Another object of the present invention is to provide a method and an apparatus for measuring the coefficient of thermal conductivity of the structural material of a building.

Still another object of the present invention is to provide a method and an apparatus for measuring the coefficient of thermal conductivity, including the step of comparison between these of unknown and known materials, wherein a known material can be selected so as to be most suitable for the characteristics of the sample.

SUMMARY OF THE PRESENT INVENTION

According to the present invention, a probe is used for picking up data concerning a coefficient of thermal conductivity of a sample. Said probe comprises, for instance, at least, material whose coefficient of thermal conductivity is known, heat means supported on the surface of said material, and a thermo-electric couple on or near said heat means. The probe is put on a sample, and the heat means and the thermo-electric couple are sandwiched between the known material and the sample. The temperature difference which is measured by said thermo-electric couple during a predetermined period provides the coefficient of thermal conductivity of the sample. Further an electric circuit means provides the direct reading of said coefficient of thermal conductivity of the sample.

Further features and advantages of the present invention will be apparent from the ensuing description with reference to the accompanying drawings to which, however, the scope of the invention is in no way limited.

BRIEF DESCRIPTION OF THE DRAWINGS

FIG. 1 is a drawing for explanation of the operational principle of the present invention;

FIG. 2(A) – FIG. 2(H) are structural embodiments of a main part of a probe of the measuring apparatus according to the present invention;

FIG. 9 is a detailed block diagram of an arithmetic circuit 46 in FIG. 8;

FIG. 10 is a curve for explanation of the circuit of FIG. 8, and;

DETAILED EXPLANATION OF THE INVENTION

Figure 3:
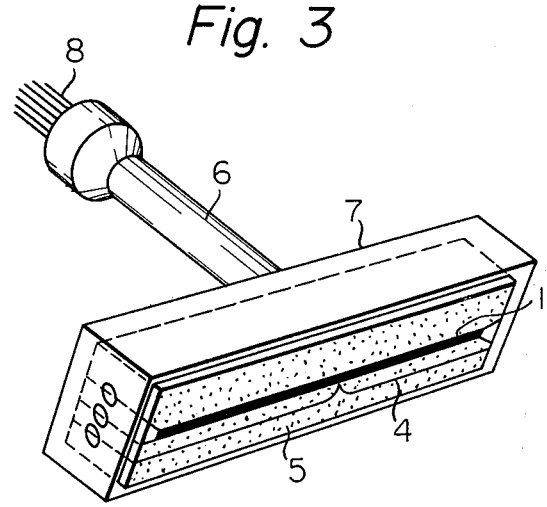
FIG. 3 shows a perspective view of a structure of one embodiment of a probe according to the present invention.

First the physical principle of the present invention will be briefly explained.

An ASTM (American Standard of Testing Materials) method (ASTM Standard D-2326-64T) is well known for measuring a coefficient of thermal conductivity of a sample. The ASTM method comprises the step of arranging a long linear heater inside of a sample of uniform material. The present invention is, in a manner of speaking, an improvement of the ASTM method.

FIG. 1 shows two kinds of materials 2 and 3, whose coefficients of thermal conductivity are different from each other, which contact each other at a boundary plane 16. A long linear heater 1 whose radius is negligible compared to its length is put on a center of said plane 16. On the condition that a heat per unit length in a unit time given on a heat line is $q$ the relationship between the heat time $t$ and temperature $T$ at a position of radius $r$ in the cylindrical coordinates system will be explained.

The equation of heat potential is as follows on the condition that the coefficients of thermal diffusion of two materials 2 and 3 in FIG. 1 are the same.

$$\frac{\delta T}{\delta t} = a \left( \frac{\delta^2 T}{\delta r^2} + \frac{1}{r} \cdot \frac{\delta T}{\delta r} \right) \tag{1}$$

where "a" is the coefficient of heat diffusion of a material and $T$ is temperature. The solution of the equation (1) is given as follows.

$$T = K_1 \int_o^t \frac{e^{-r^2/4at}}{t} dt \qquad (2)$$

$$= K_2[I(rn)] \qquad 3.$$

where $n = 1/\sqrt{4at}$ $$I(rn) = C - \ln(rn) + \frac{(rn)^2}{2} - \frac{(rn)^4}{8} + \ldots \qquad (4)$$

and $C$, $K_1$ and $K_2$ are constant. If $(rn)$ is extremely small, terms with squared or higher powers of $(rn)$ can be neglected, and the following equation (5) gives an approximate solution of the equation (1).

$$T = K_2 \left[ C - \ln\left(\frac{r}{\sqrt{4at}}\right) \right] \qquad (5)$$

Since the above equation (5) always satisfies the heat boundary condition in material 2 and material 3, a value of $K_2$ in equation (5) is next determined.

If the heat capacity of a heater itself is neglectably small and a radius of a heater is $r_0$, then the following equation holds good at the point $r = r_0$.

$$\left( \pi r \lambda_1 \frac{\delta T}{\delta r} + \pi r \lambda_2 \frac{\delta T}{\delta r} \right)_{r = r_o} = q \qquad (6)$$

where $\lambda_1$ and $\lambda_2$ are the coefficients of thermal conductivity of material 2 and material 3, respectively. The value of $K_2$ is obtained by solving equation (6).

$$K_2 = \frac{q}{\pi(\lambda_1 + \lambda_2)}$$

The above value $K_2$ is substituted in the equation (5), $$T = \frac{q}{\pi(\lambda_1 + \lambda_2)} \left[ C - \ln\left(\frac{r}{\sqrt{4at}}\right) \right] \qquad (7)$$

Equation (7) can be changed to equation (8) by substituting temperatures $T_1$ and $T_2$ at time $t_1$ and $t_2$, respectively.

$$\lambda_2 = \frac{q \ln\left(\frac{t_2}{t_1}\right)}{2\pi(T_2 - T_1)} - \lambda_1 \qquad (8)$$

As is apparent from the equation (8), the coefficient of thermal conductivity $\lambda_2$ of a material can be measured if the coefficient of a thermal conductivity $\lambda_1$ of the other material is known.

Accordingly, the measuring apparatus of the present invention comprises, at least, a block, made of material whose coefficient of thermal conductivity is known, a heater and a thermo-electric couple, which are combined so as to satisfy the precondition of above equation (8). In some cases the heater can double as means for measuring the temperature, and the thermo-electric couple can be removed.

It should be understood from equation (8) that the coefficient of thermal conductivity $\lambda_1$ should be as small as possible in order to measure $\lambda_2$ accurately, since the value of $\lambda_1$ changes little from temperature and/or humidity change in the atmosphere.

The equation (8) must be sometimes modified when a particular relationship of positions between a heater and a thermo-electric couple, or a particular connection with a heater and a known or unknown material occurs. In that case, the following equation (9), corresponding to equation (8), is useful.

$$\lambda_2 = K \cdot \frac{q \ln\left(\frac{t_2}{t_1}\right)}{2\pi(T_2 - T_1)} - \lambda_1 \qquad (9)$$

where $K$ is a constant defined by a particular measuring apparatus, and $K$ can be decided by calculating $$(\lambda_2 + \lambda_1) \bigg/ \left[ \frac{q \ln\left(\frac{t_2}{t_1}\right)}{2\pi(T_2 - T_1)} \right] \qquad (10)$$

when a material whose coefficient of thermal conductivity is known is measured by the particular apparatus.

FIGS. 2(A) – 2(H) show some embodiments of the main part of a probe of a measuring apparatus according to the present invention.

In FIG. 2(A), a linear heater 1 has a relatively large electrical resistance like a nichrome wire. Means 4 for measuring temperature of said heater 1 is directly attached to said heater at about a middle point of said heater 1. Said means 4 may be a thermo-electric couple whose diameter is far smaller than that of the heater 1, a thermister or a small volume resistance for temperature measurement. For example, said means 4 is a CA type thermo-electric couple which is welded to the heater 1 at point 20. CA type thermo-electric couple is a kind of a thermometer to operate on the basis that the electromotive force is proportional to the temperature difference between a hot junction and a cold junction. The relationship between the electromotive force and the temperature difference of CA thermo-couple is well known in the art. Said heater 1 and thermo-couple 4 are positioned on the surface of a block 5 whose shape is a rectangular prism. The block 5 is made of resilient material like felt or cork in order to provide close contact between a sample and said block 5. The coefficient of thermal conductivity of the block 5 should be, of course, known and its value should be preferably as small as possible. The size of block 5 should be large enough to satisfy the pre-condition of the principal of FIG. 1, for instance, about 50 mm wide, 150 mm long and 25 mm thick.

FIG. 2(B) is a second embodiment of a probe according to the present invention. The structure of FIG. 2(B) is similar to that of FIG. 2(A) and the only difference between them is that the junction 20 of means 4 for measuring temperature in FIG. 2(B) does not contact the heater 1 but is positioned near the heater 1, while the junction 20 of FIG. 2(A) is attached to the heater 1. Accordingly, in FIG. 2(B) it is unnecessary to weld means 4 to a fine heater and thus, the probe of FIG. 2(B) is easily manufactured. The equation (9) is more suitable for the embodiment of FIG. 2(B).

FIG. 2(C) shows another embodiment of a probe according to the present invention. The strucutre of FIG. 2(C) is similar to that of FIG. 2(A), but in FIG.

2(C) means 4 for measuring temperature doubles as a heater. That is to say, an alternating current flows through and heats a thermo-couple and its wire. And the change of temperature of the thermo-couple is measured by the thermo-couple. After that, the coefficient of thermal conductivity of a sample is calculated using the equation (8).

FIG. 2(G) shows another embodiment of a probe according to the present invention. In FIG. 2(G), a heater 1 has a pair of lead wires 35 spaced a predetermined length apart on said heater 1 for measuring the voltage drop in said heater 1. The heater 1 is made of, for instance, platinum wire. When a current flows through said heater 1, the electric resistance of said heater 1 changes due to its temperature change and, thus, the resistance and the temperature of the heater 1 can be obtained by measuring the current in said heater 1 and the voltage drop between said pair of leads 35. After that, the coefficient of thermal conductivity of the sample is calculated using the equation (8). The feature of FIG. 2(G) is that the heater doubles as means for measuring the temperature, and the thermo-couple is removed.

In FIGS. 2(A) – 2(C) and 2(G), a probe which does not have a block 5 is possible. In that case, reference material whose coefficient of thermal conductivity is known can be provided as an attachment each time measurement is performed and thus, the most suitable reference material can be selected for each sample. FIGS. 2(D), 2(E), 2(F) and 2(H) show four embodiments which do not have a block 5. In these embodiments, both a heater 1 and means 4 for measuring temperature are mounted on a support means 21 which is a thin plane with an extremely small coefficient of thermal conductivity. Many modifications of the support means 21 will occur to those skilled in the art. For example, a string or spring means instead of the plane support means can support the heater 1 and means 4. The embodiment of FIG. 2(D) corresponds to that of FIG. 2(A), in which a junction 20 is directly attached to a heater 1. The embodiment of FIG. 2(E) corresponds to that of FIG. 2(B), in which a junction 20 is positioned near a heater 1, the embodiment of FIG. 2(F) corresponds to that of FIG. 2(C), in which a junction 20 and its wire double as a heater, and the embodiment of FIG. 2(H) corresponds to that of FIG. 2(G), in which a heater doubles as means for measuring temperature. In the embodiments of FIGS. 2(D), 2(E), 2(F) and 2(H), a heater and/or a thermo-couple are surrounded by reference material and a sample in the actual measuring operation.

The shape of the heater 1 in FIGS. 2(A) – 2(H) is preferably band shape with a rectangular cross section instead of a circular cross section. Thus, the contact condition of the probe with a sample is improved, and an accurate result is obtained from equations (8) or (9). A band type heater, for instance, of 1 mm width, 70 $\mu$m thickness and 150 mm long made of nichrome or platinum is preferable.

FIG. 3 shows one embodiment of a whole view of a probe including one of the structures in FIGS. 2(A) – FIG. 2(C) and FIG. 2(G). In FIG. 3, reference material 5, a heater 1 and a thermo-couple 4 are covered with cover means 7, to which a stick 6 is connected. At the end of the stick 6, a plug 8 to which a heater 1 and a couple 4 are electrically connected is attached.

Figure 4:
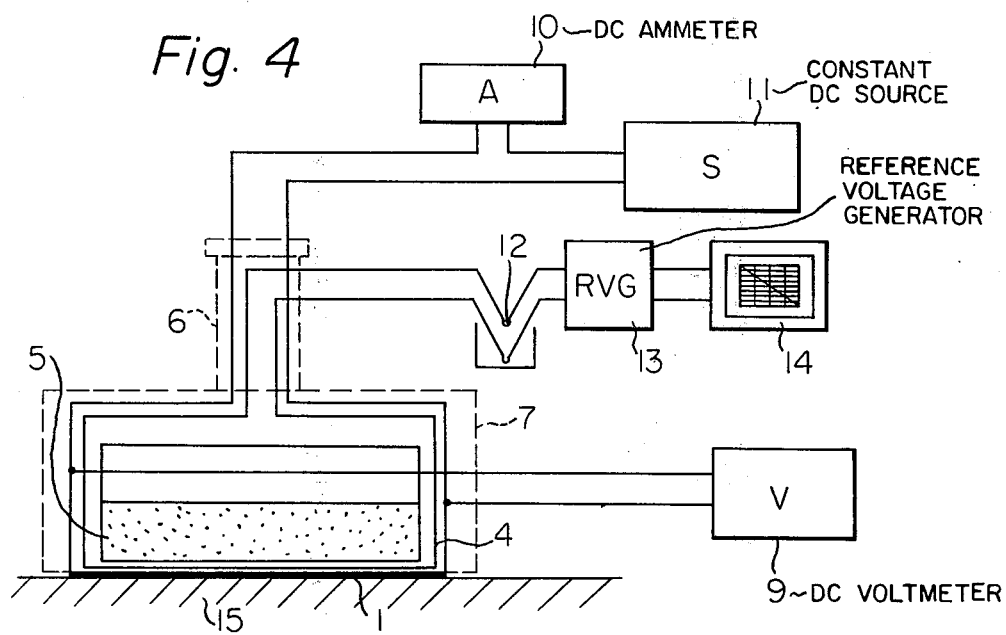
FIG. 4 shows one embodiment of a circuit arrangement of the present apparatus.

FIG. 4 shows a block diagram of an electrical circuit for the probe of FIGS. 2(A), 2(B), 2(D) and 2(E). In FIG. 4 a probe having reference material 5, whose coefficient of thermal conductivity is $\lambda_1$, a heater 1 and a thermo-couple 4 covered with cover means 7, is put on a sample 15 so as to place said heater 1 and couple 4 between said reference material 5 and the sample 15. The heater 1 is energized by a regulated constant current source 11. The current through the heater is measured by a DC ammeter 10 and the voltage between two terminals of the heater is measured by a DC voltmeter 9. The power applied to the heater 1, or the calories $q$ in equation (8) generated by the heater 1 per unit length in a unit of time can be calculated from the readings of said meters 9 and 10. The data concerning the temperature of the heater 1 is picked up by a CA thermo-electric couple 4, whose output voltage is applied to a pen-recorder type voltmeter 14 through a cold junction 12 and a reference voltage generator 13. The generator 13 operates so as to subtract a predetermined value from the output voltage of said CA couple 4 and, thus, only the deviation of the output voltage of said couple 4 is applied to the recorder 14. It should be easily understood that the coefficient of thermal conductivity $\lambda_2$ of the sample 15 can be calculated from the equation (8) by substituting the relationship between the temperature $T_1$, $T_2$ and time $t_1$, $t_2$.

Figure 5:
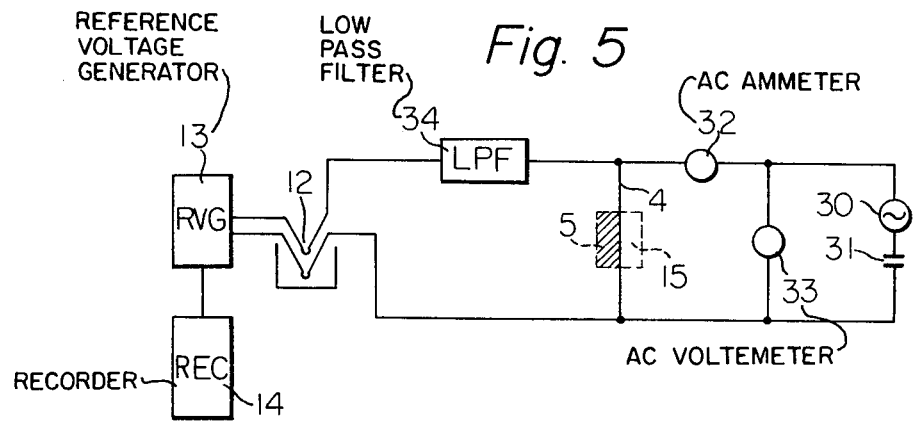
FIG. 5 shows the other embodiment of a circuit arrangement of the present apparatus.

FIG. 5 shows another block diagram of an electrical circuit, which can be used with a probe of FIG. 2(C) or FIG. 2(F). In FIG. 5, a thermo-electric couple 4 is put between reference material 5 whose coefficient of thermal conductivity is $\lambda_1$ and a sample 15 whose coefficient of thermal conductivity is unknown. The thermo-electric couple 4 and its related wire are heated by alternating current from an alternating source 30 through a capacitor 31. A commercial source with 50 or 60 Hz can be used as the alternating source 30. The power applied to the heater or couple 4 is calculated from the readings of an alternating current ammeter 32 and an alternating current voltmeter 33 and, thus, the calories generated by the heater or couple 4 is calculated. The value of the DC thermo-electro motive force generated by said heater or couple 4 is applied to a pen-recorder type DC voltmeter 14 through a low pass filter (LPF) 34, a cold junction compensator 12 and a reference voltage 13. Said recorder 14 provides, of course, the reading of the deviation of temperature at the couple 4. Said low pass filter (LPF) 34 prevents the alternating current from flowing to the DC recorder 14.

Figure 11:
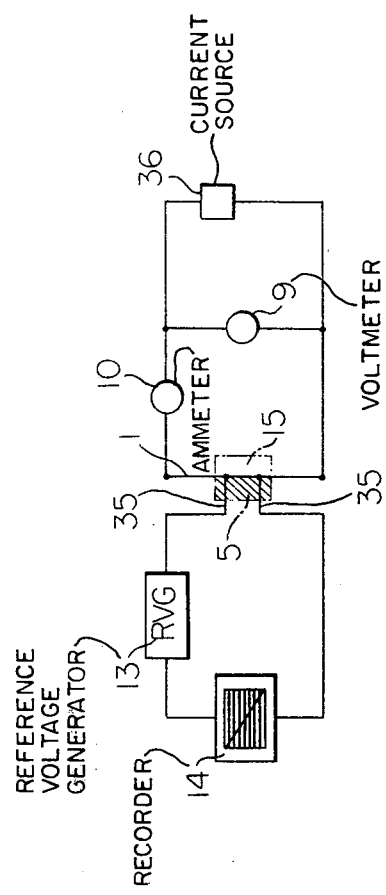
FIG. 11 shows another embodiment of a circuit arrangement of the present apparatus.

FIG. 11 shows another block diagram of an electrical circuit, which can be used with the probe of FIG. 2(G) or FIG. 2(H). In FIG. 11, only a heater 1 is placed between reference material 5 whose coefficient of thermal conductivity is known and a sample 15 whose coefficient of thermal conductivity is unknown. The heater 1 is heated by an electrical current from a source 36. The power applied to the heater 1 is calculated from the readings of an ammeter 10 and a voltmeter 9, and the amount of calories generated by the heater 1 is calculated from said power. A value $R$ of resistance of the heater 1 at temperature $T$ relates to the temperature of the heater itself and is shown as follows.

$$R = R_o (1 + \beta T)$$

where $R_o$ and $\beta$ are constants, $T$ is the temperature of the heater 1, and $R$ is the ratio of the current flowing in the heater 1 and the voltage drop between a pair of leads 35, which is read from a pen-recorder type voltmeter 14 through a reference voltage generator 13. It should be understood from said equation that the value $(T_2 - T_1)$ in the equation (8) is given by;

$$\frac{(V_2 - V_1)}{\beta R_o I};$$

where $U_1$ and $U_2$ are voltages between the pair of leads 35 and correspond to the temperatures $T_1$ and $T_2$, respectively, and $I$ is the value of electrical current in the heater 1. As is apparent from the above explanation, the coefficient of thermal conductivity can be obtained by the circuit of FIG. 11 which has no electrical thermo-couple.

Figure 6:
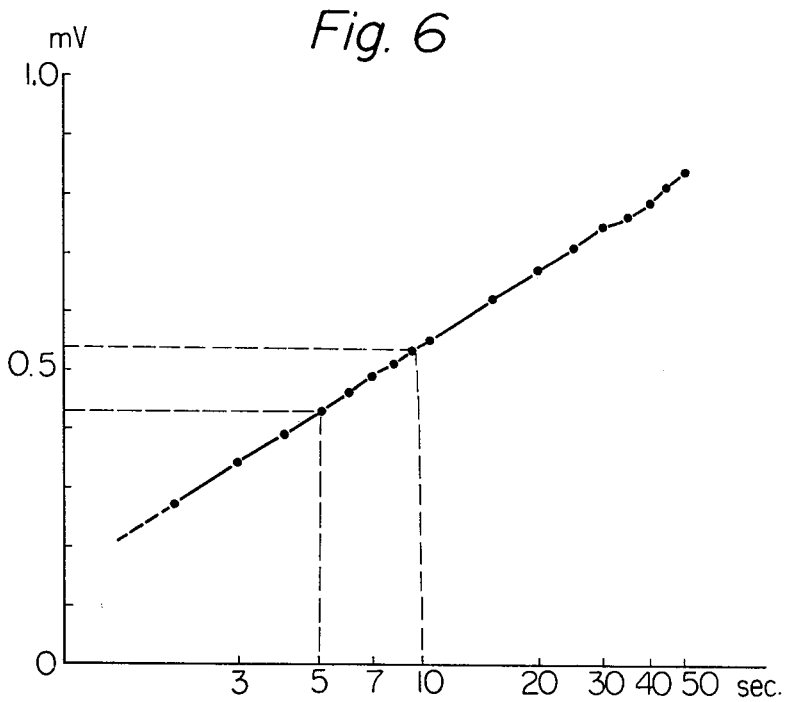
FIG. 6 shows a curve of measured temperature according to the present invention.

FIG. 6 shows an embodiment of a curve measured by the apparatus according to the present invention. In FIG. 6, the horizontal axis is a logarithmic scale in seconds, and the vertical axis is a regular scale in mV. The curve in FIG. 6 shows substantially the deviation of the temperature measured by a CA thermo-couple. In FIG. 6, the band type heater and the thermo-couple are spot-welded, the reference material is asbestos whose coefficient of thermal conductivity $\lambda_1$ is 0.045 Kcal/m.-hour.°C, the sample is adiabatic brick, the calories generated by the heater is 4.16 Kcal/h.m and room temperature is 25°C. In FIG. 6, output voltages at time $t_1 = 5$ seconds and $t_2 = 10$ seconds are 0.43 mV and 0.55 mV, respectively and thus, the deviation of output voltage is $0.55 - 0.43 = 0.12$ mV, which corresponds to 2.9°C in CA thermo-couple.

Accordingly, $K = 1.13$
$q = 4.16$ (Kcal/h.m)
$t_2/t_1 = 10/5 = 2$
$T_2 - T_1 = 2.9°C$ and
$\lambda_1 = 0.045$ (Kcal/m.hour. °C)

are substituted in the equation (9) and the coefficient of thermal conductivity $\lambda_2$ of adiabatic brick is given as follows.

$$\lambda_2 = 0.13 \text{ Kcal/m.hour.°C}$$

Figure 7:
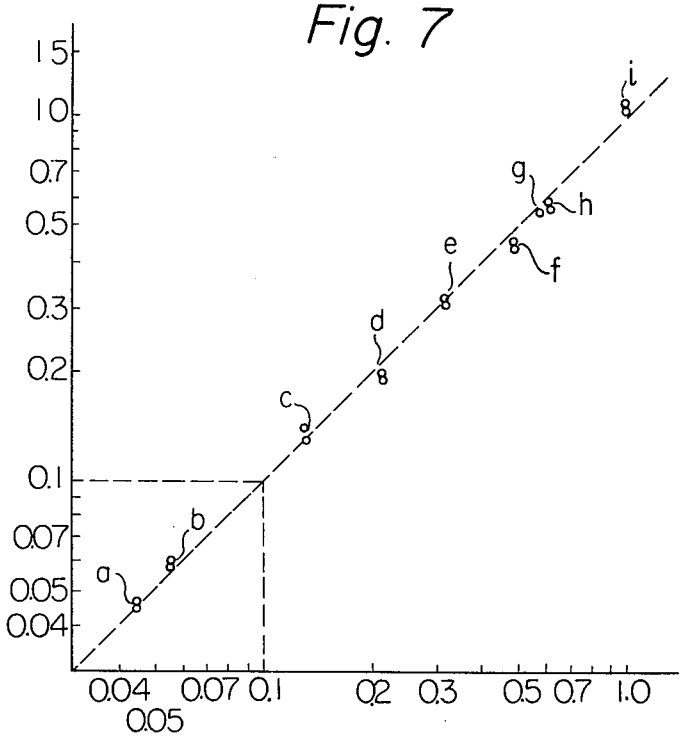
FIG. 7 shows a curve of the relationships of measured values between the present invention and prior art (the ASTM Standard D-2326-64T)

FIG. 7 shows a curve of the relationships between the measured results by the prior ASTM method (D-2326-64T) and by the present invention. In FIG. 7, the horizontal axis shows coefficient of thermal conductivity $\lambda_o$ of some material measured by the prior ASTM method by putting $\lambda_1 = \lambda_2 = \lambda_0$ in the equation (8), and the vertical axis shows the coefficient of thermal conductivity $\lambda_m$ of the same material measured by the present invention. In the curve of FIG. 7, the material of point $a$ is asbestos, of point $b$ is cork, of point $c$ is B1 brick, of point $d$ is epoxy resin, of point $e$ is C1 brick, of point $f$ is red brick, of point $g$ is gum, of point $h$ is shamote brick, and of point $i$ is opaque quartz glass. As is apparent for FIG. 7, the error of the measured value according to the present invention is less than 5 percent, and the reproducibility of the measured value is very good. The curve of FIG. 7 shows that the coefficient of thermal conductivity of any material can be measured even when $\lambda_1$ and $\lambda_2$, and further, the coefficients of heat diffusion between the reference material and a sample, are different from each other, and that the present invention is extremely useful.

Figure 8:
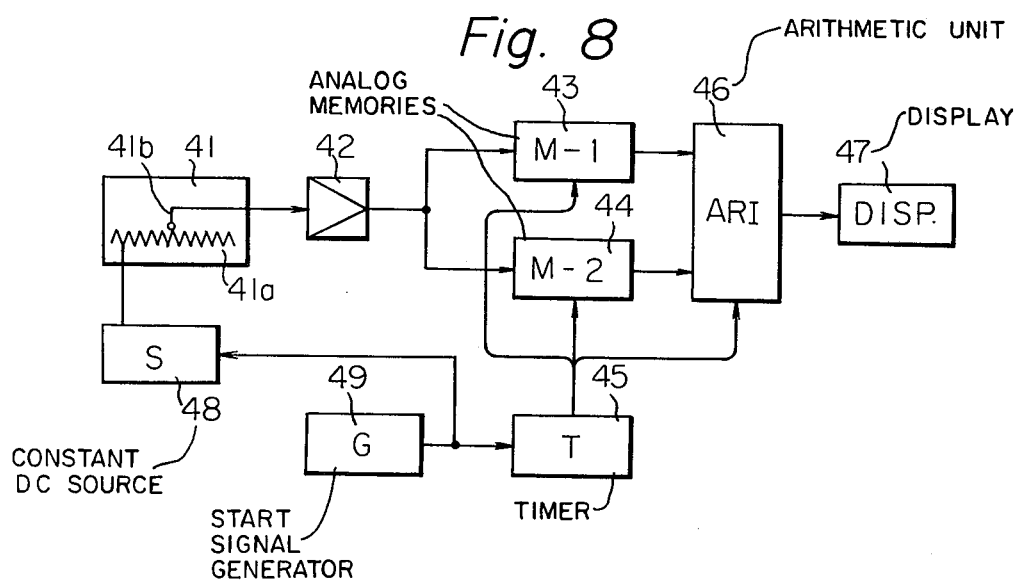
FIG. 8 is a block diagram of a circuit for direct reading of the measured coefficient of thermal conductivity.

FIG. 8 shows a block diagram of another embodiment of the electrical circuit according to the present invention. The circuit of FIG. 8 provides a direct reading of the measured coefficient of thermal conductivity without any calculation. In FIG. 8, a probe 41 has a heater 41a and a thermo-electric couple 41b and may be any of the structures of FIGS. 2(A) – 2(H). The output voltage of the thermo-couple of the probe 41 is applied to the first and second analog memories 43 and 44 through a pre-amplifier 42. The memories 43 and 44 store analog voltage temporarily using capacitance. A timer circuit 45 provides timing signals $t_1$ and $t_2$. The duration between $t_1$ and $t_2$ is predetermined. The timing signals $t_1$ and $t_2$ from the timer circuit 45 are applied to said memories 43, 44 and an arithmetic unit 46. The memories 43 and 44 store the instantaneous voltages relating to the measured temperature at $t_1$ and $t_2$, respectively. The output voltages $U_1$ and [$V_2$ of the memories 43 and 44 are applied to the arithmetic unit 46, which calculates the coefficient of thermal conductivity according to the equation (8) or (9). The output of said arithmetic unit 46 which corresponds to the coefficient of thermal conductivity is applied to a display unit 47 causing the direct display of the measured coefficient of thermal conductivity. The display unit 47 may be either an analog type ammeter or a digital type display unit. A constant current source 48 causes the heater 41a to generate predetermined calories in a unit time by supplying regulated electrical power. A start signal generator 49 provides the start signal for starting the operation of the apparatus. When the start signal occurs the timer circuit 45 is started for measuring time $t_1$ and $t_2$, and the electrical power is supplied to the heater 41a from the current source 48. When the timer circuit 45 generates the second timing signal $t_2$, the arithmetic unit 46 starts to calculate the coefficient of thermal conductivity.

FIG. 9 shows a detailed block diagram of the arithmetic unit 46 in FIG. 8. Output voltages $V_1$ and $V_2$ relating to the temperature of the heater 41a at time $t_1$ and $t_2$ are applied to a feedback amplifier 50 through resistors 54 and 55. The structure having the amplifier 50 and resistors 54 and 55 composes a subtraction circuit and provides $\Delta V = V_2 - V_1$ at its output. A value $\Delta V$ is applied to one input of a multiplier 53, the other input of which is fed by the output of a feedback amplifier 51. Thus the structure of the multiplier 53, the amplifier 51 and resistors 57 and 58 composes a divider, which provides $\alpha/\Delta V$ at its output. A value $\alpha$ is constant and is applied to the divider through the resistor 58. $\alpha/\Delta V$ represents $$\frac{q \ln\left(\frac{t_2}{t_1}\right)}{2\pi(T_2 - T_1)}$$

in equation (8) or $$K \frac{q \ln\left(\frac{t_2}{t_1}\right)}{2\pi(T_2 - T_1)}$$

in equation (9), because $K$, $q$, $t_1$ and $t_2$ are constant in the particular measuring apparatus, and $\Delta V = (V_2 - V_1)$ corresponds to the temperature difference $T_2 - T_1$. Therefore $$\frac{q \ln\left(\frac{t_2}{t_1}\right)}{2\pi}$$

or $$K \frac{q\ln(\frac{t_2}{t_1})}{2\pi}$$

is constant and can be replaced by $\alpha$. A voltage proportional to $\alpha$ is applied to the divider through the resistor 58. Thus said equations (8) and (9) can be replaced as follows.

$$\lambda_2 = \frac{\alpha}{\Delta V} \lambda_1$$

The subtraction circuit having resistors 59 and 60 and a feedback amplifier 52 performs the subtraction $\alpha/\Delta V - \lambda_1$ and provides $\lambda_2$ at its output.

The operation of the circuit of FIG. 8 will now be explained. When the start signal generator 49 generates a start pulse, the timer circuit 45 starts the operation and the current source 48 starts to supply electrical power to the heater 41a. Then the heater 41a of the probe 41 generates calories and supplies calories to a sample. The temperature of the heater 41a rises gradually as shown in FIG. 10, in which the horizontal axis shows time and the vertical axis shows voltage or temperature. The rising rate of the curve in FIG. 10 relates to the coefficient of thermal conductivity of the sample. The temperature of the heater 41a is measured by the thermo-couple 41b, which provides output voltage relating to the temperature to the memories 43 and 44. The memory 43 stores the analog voltage $V_1$ at time $t_1$ and the memory 44 stores the analog voltage $V_2$ at time $t_2$. The time $t_1$ and $t_2$ are, of course, defined by the timer circuit 45. The arithmetic unit 46 starts to operate, triggered by the output signal from the timer circuit 45, just after memories 43 and 44 have finished storing $V_1$ and $V_2$, respectively and, thus, the arithmetic unit 46 provides an output signal, with an amplitude proportional to the coefficient of thermal conductivity $\lambda_2$ of the sample. The value of $\lambda_2$ is displayed directly on a display unit 47.

The circuit of FIG. 8 can be made of electronic components, and will work from a commercial electric power source or a portable battery.

As mentioned above in detail, the present invention provides an apparatus for measuring the coefficient of thermal conductivity which is of small size and light weight. Further, according to the apparatus of the present invention, such measurement can be accomplished in a very short time. Additionally, the present apparatus provides a measuring apparatus for not only coefficient of thermal conductivity but also coefficient of heat diffusion.

Although the above invention has been described with reference to specifically disclosed embodiments, the invention is not to be so limited. Rather, the invention is deemed to include obvious modifications and alterations to the specific embodiments above described.

Other obvious modifications and alterations within the ability of a worker skilled in the art are contemplated in this invention. The precise scope of this invention is defined in the following claims.

What we claim is:

1. Apparatus for measuring the thermal conductivity of a sample comprising a rectangular cover means having an open end, a stick, one end of which is connected to said cover means, a reference material inserted in said cover means so that the flat surface of said reference material is on said open end of said cover means, the thermal conductivity of said reference material being known, a long linear electric heater having a resistance $R=R_o (1 + \beta T)$ mounted on the surface of said reference material, said electric heater being connected to a current source, a thermo-electric couple connected to the surface of the middle part of said heater, said thermo-electric couple being electrically connected to a meter to measure temperature, a plug attached to the end of said stick for electrically connecting said heater and said thermo-electric couple to the current source and to the meter, where $R_0$ and $\beta$ are constants and $T$ is an average temperature of the electric heater, said thermo-electric couple measuring the temperature of said heater at least at two predetermined different times before the reference-sample-heater system reaches thermal equilibrium.

2. Apparatus as described in claim 1 and further comprising means for developing the thermal conductivity of said sample according to the measured data in accordance with the following relation:

$$\lambda_2 = K \frac{q\ln\left(\frac{t_2}{t_1}\right)}{2\pi(T_2-T_1)} \lambda_1$$

where $R_0$, $\beta$, $K$ and $\lambda_1$ are constants, $T$ is $T_1 + T_2/2$, $q$ is the heat per unit length in a unit time in said long linear electric heater, $T_1$ and $T_2$ are the measured temperture of said heater at time $t_1$ and $t_2$, respectively, and $\lambda_2$ is the thermal conductivity of said sample.

3. Apparatus for measuring the thermal conductivity of a sample comprising a rectangular cover means having an open end, a stick, one end of which is connected to said cover means, a reference material inserted in said cover means so that the flat surface of said reference material is on said open end of said cover means, the thermal conductivity of said reference material being known, a long linear electric heater having a resistance $R=R_0 (1 + \beta T)$ mounted on the surface of said reference material, said electric heater being connected to a current source, a thermo-electric couple connected to the surface near the middle part of said heater, said thermo-electric couple being electrically connected to a meter to measure temperature, a plug attached to the end of said stick for electrically connecting said heater and said thermo-electric couple to the current source and to the meter, where $R_0$ and $\beta$ are constants and $T$ is an average temperature of the electric heater, said thermo-electric couple measuring the temperature of said heater at least at two predetermined different times before the reference-sample-heater system reaches thermal equilibrium.

4. Apparatus as described in claim 3 and further comprising means for developing the thermal conductivity of said sample according to the measured data in accordance with the following relation:

$$\lambda_2 = K \frac{q\ln\left(\frac{t_2}{t_1}\right)}{2\pi(T_2-T_1)} \lambda_1$$

where $R_0$, $\beta$, $K$ and $\lambda_1$ are constants, $T$ is $T_1+T_2/2$, $q$ is the heat per unit length in a unit time in said long linear electric heater, $T_1$ and $T_2$ are the measured temperature of said heater at times $t_1$ and $t_2$, respectively, and $\lambda_2$ is the thermal conductivity of said sample.

* * * * *